US009799188B2

(12) United States Patent
Lee et al.

(10) Patent No.: US 9,799,188 B2
(45) Date of Patent: *Oct. 24, 2017

(54) INTELLIGENT EARPLUG SYSTEM

(71) Applicant: Hush Technology Inc., San Diego, CA (US)

(72) Inventors: Daniel Lee, Framingham, MA (US); Chesong Lee, Framingham, MA (US); Dongyeup D. Synn, Los Angeles, CA (US)

(73) Assignee: Hush Technology Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/352,034

(22) Filed: Nov. 15, 2016

(65) Prior Publication Data

US 2017/0061760 A1    Mar. 2, 2017

Related U.S. Application Data

(63) Continuation of application No. 15/106,989, filed as application No. PCT/US2015/017165 on Feb. 23, 2015.

(Continued)

(51) Int. Cl.
| | |
|---|---|
| *H04R 25/00* | (2006.01) |
| *G08B 21/02* | (2006.01) |
| *H04R 1/10* | (2006.01) |
| *A61M 21/00* | (2006.01) |
| *G08B 3/10* | (2006.01) |
| *G08B 21/04* | (2006.01) |

(Continued)

(52) U.S. Cl.
CPC ......... *G08B 21/0208* (2013.01); *A61M 21/00* (2013.01); *G08B 3/1025* (2013.01); *G08B 21/0446* (2013.01); *G08B 21/0453* (2013.01); *H04R 1/1016* (2013.01); *H04R 1/1083* (2013.01); *A61B 5/01* (2013.01); *A61B 5/024* (2013.01); *A61B 5/067* (2013.01); *A61B 5/4809* (2013.01); *A61B 5/6817* (2013.01); *A61M 2021/0027* (2013.01); *A61M 2021/0083* (2013.01); *H04R 2400/03* (2013.01); *H04R 2420/07* (2013.01)

(58) Field of Classification Search
CPC   H04R 1/1016; H04R 1/1025; H04R 2420/07; H04R 2460/07; G06F 3/165; H04W 68/00
USPC ......................................................... 381/380
See application file for complete search history.

(56) References Cited

U.S. PATENT DOCUMENTS

| | | | |
|---|---|---|---|
| 2008/0019554 A1* | 1/2008 | Krywko | H04R 1/1058 381/380 |
| 2008/0187163 A1* | 8/2008 | Goldstein | H04R 25/70 381/380 |

(Continued)

*Primary Examiner* — Sean H Nguyen
(74) *Attorney, Agent, or Firm* — Brian M. Dingman; Dingman IP Law, PC

(57) ABSTRACT

The present teachings disclose methods and apparatuses for an intelligent, wireless earplug system comprising a speaker, an earplug, an electronics base, and a cable. The earplug fits into a user's ear canal and is operatively connected to a smart device, such as a smart phone, to intelligently transmit sounds from the smart device to the earplugs in a manner selected by the user, such as for example transmitting binaural beats to the earplugs to facilitate sleep.

4 Claims, 1 Drawing Sheet

Related U.S. Application Data

(60) Provisional application No. 61/943,433, filed on Feb. 23, 2014.

(51) Int. Cl.
    *A61B 5/01*     (2006.01)
    *A61B 5/024*     (2006.01)
    *A61B 5/06*     (2006.01)
    *A61B 5/00*     (2006.01)

(56) References Cited

U.S. PATENT DOCUMENTS

| | | | |
|---|---|---|---|
| 2008/0298308 A1* | 12/2008 | Hannu | H04W 4/10 370/328 |
| 2012/0027215 A1* | 2/2012 | Sim | H04R 1/1041 381/55 |
| 2013/0156239 A1* | 6/2013 | Pedersen | H04R 25/43 381/315 |
| 2013/0244633 A1* | 9/2013 | Jacobs | H04W 68/00 455/415 |
| 2015/0245129 A1* | 8/2015 | Dusan | H04R 1/1083 381/71.6 |

* cited by examiner

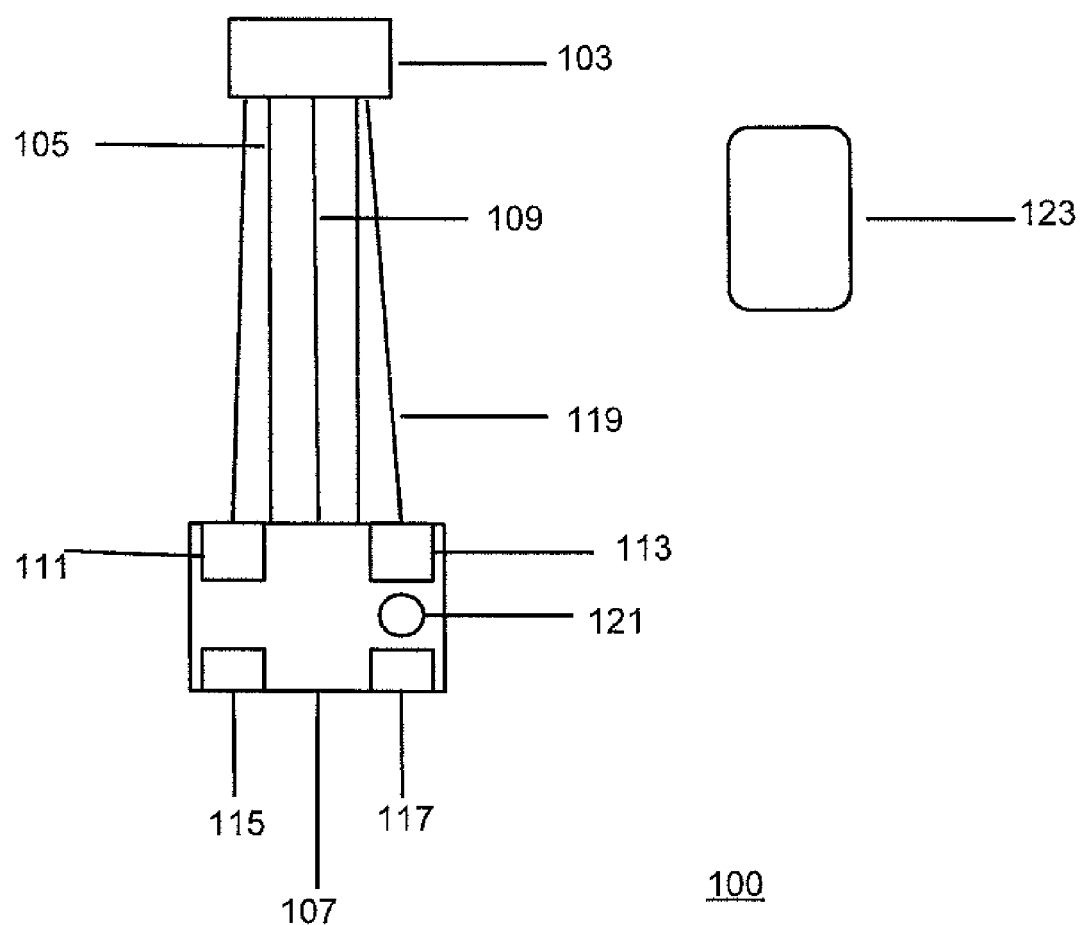

INTELLIGENT EARPLUG SYSTEM

PRIORITY CLAIM

This application is a Continuation of U.S. application Ser. No. 15/106,989, filed Jun. 21, 2016, which is a national-phase entry of Patent Cooperation Treaty application PCT/U.S. 2015/017165, filed Feb. 23, 2015, which claims the benefit of priority to earlier filed U.S. Provisional Patent Application, having Ser. No. 61/943,433, filed Feb. 23, 2014, entitled, "INTELLIGENT EARPLUG SYSTEM", by Daniel Keewoong Lee, Dongyeup Daniel Synn, and Daniel Chesong Lee.

BACKGROUND OF THE INVENTION

The present teachings disclose a method, apparatus, system and article of manufacture for an earplug device that communicates with at least one electronic device. The present disclosure broadens the functionality of a basic earplug into a "smart" earplug. "Smart" means the disclosed earplug device has advanced computing capabilities and connectivity. The present teachings disclose a speaker, sensors, a wireless transmission module, a battery, and a processor integrated into an earplug device that communicates wirelessly with at least one electronic device.

The present teachings describe how the user can go to sleep wearing the earplug device and still hear an alarm. Further, the alarm that awakens the user is not audible to other people, thereby not disturbing others. The present teachings disclose how the alarm gradually increases in volume, eventually reaching dB levels that will most likely awaken the user. If the user does not wake up for a pre-determined time, the earplug device triggers an alarm from the at least one electronic device to ring as a backup measure. The earplug device also has at least one biometric sensor, such as an accelerometer, that tracks motion of the user at night. This allows for tracking of sleep cycles of the user and allows for a "smart wake up" function. The "smart wake up" function will prevent the alarm from sounding while the user is in rapid eye movement ("REM") sleep to make it easier to wake up.

DESCRIPTION OF THE RELATED ART

Earplugs are a common remedy for people trying to sleep in noisy environments but a major limitation is that a user cannot reliably wake up to alarms. Several people have attempted to solve this problem but none have brought the concept to market. This was because earlier earplug alarm clocks lacked in major features that could give it a favorable product market fit. For example, the hassle in having to charge an earplug alarm clock every day is a major deterrent for regular usage.

BRIEF DESCRIPTION OF THE DRAWINGS

Embodiments of the present disclosure will be more readily understood by reference to the following figures, in which like reference numbers and designations indicate like elements.

FIG. 1 illustrates an earplug apparatus, wherein a speaker, sensors, and a wireless transmission module communicate with at least one electronic device, according to one embodiment of the present teachings.

DETAILED DESCRIPTION

It will be appreciated that the earplug device may be used in a variety of settings. The following list is not an exhaustive list but is meant to assist in understanding the earplug device. As an example, students in noisy college environments who have to wake up and not disturb roommates may wear the earplug device. Another example applies to public transit commuters who take a nap and have to wake up when they approach their designated stop areas. Other examples are couples with a snoring partner where the other partner has to wake up at a certain time; people who desire to monitor their sleep; people who choose to use smart technology to optimize their sleep; people who have trouble sleeping and use binaural/isochronic/monaural beats to help them fall asleep; people who take a nap in quiet locations and not want to disturb others with their alarm, e.g., students studying at a library. The earplug device may also take advantage of additional technology available in the smartphone platform. For example, the earplug device may use a smartphone's GPS to track when the user nears a location and to sound the alarm accordingly.

The earplug device also implements the use of binaural beats by playing slightly different frequencies in each ear that causes a beat to be formed in the user's head. This causes "brain entrainment," a process whereby an operating frequency of a brain aligns itself with a binaural beat formed. Lucid dreaming communities value binaural beats to help them achieve an appropriate state of mind. The lucid dreaming communities may find wearing the earplug device useful because it may trigger a soft alarm during deep REM cycle; this is done so that the user is notified inside of her dream that she is dreaming. Brain entrainment helps induce sleep. Brain entrainment may also be used with the earplug device to stimulate other desired brain states, such as focus and alertness. The earplug device may also utilize received signal strength indicator ("RSSI") proximity sensing to allow for tracking of the earplug device if misplaced. RSSI measures power present in a received radio signal.

The present disclosure overcomes a myriad of limitations due to an inability to hear certain sounds, for example, an alarm, while wearing earplugs. The present disclosure has additional functionalities. The embodiments set forth are offered to assist in understanding other functionalities of the earplug device and do not represent an exhaustive list. In one embodiment, the earplug device may set iOS applications to send notifications other than alarm clocks. "iOS" is a mobile operating system previously known as iPhone operating system. The user may choose from a list of contacts to have the earplug device send her a notification when certain people call. In one embodiment, the earplug device may connect to other devices, such as a baby monitor. The baby monitor may trigger the alarm to alert a mother to the needs of her baby. In one embodiment, the earplug device includes an ear bone microphone for applications in allowing for easy to hear phone calls in loud environments. For example, a construction worker may use the earplug device in the loud environments. Noise reduction component of the earplugs may allow the user to hear conversations clearly as an ear bone conduction component allows a voice of a user to come through clearly. In one embodiment, the earplug device may stream music into speakers, which may be set to play a preset playlist for a pre-determined amount of time at night.

The present teachings disclose how users may enjoy benefits of noise masking earplugs while utilizing functions enabled by a speaker and sensors. The present teachings describe how to make and use a high technology earplug device that is not currently available in the art.

Referring now generally to FIG. 1, one embodiment of an earplug apparatus 100 is disclosed. The earplug apparatus 100 generally comprises a speaker 103, an earplug 105, an electronics base 107, a cable 109, sensors 111, a wireless transmission module 113, a battery 115, a processor 117, a replaceable foam earplug 119, an accelerometer 121, and at least one electronic device 123.

Connecting the speaker 103 to the electronics base 107 with the cable 109 may allow the speaker 103 to be easily detached from the electronics base 107. In one embodiment, the cable 109 may be a threaded cable. Easy detachment of the speaker 103 from the electronics base 107 is useful because the earplug 105 may be easily replaced. When the speaker 103 is removed from the electronics base 107, the earplug 105 can be slipped off a wiring of the speaker 103, replaced with a new one, and then put back onto the electronics base 107.

The speaker 103 may be designed with a variety of different technologies. In one embodiment, the earplug device may utilize a piezoelectric transducer, which is a device that converts electrical pulses to mechanical vibrations. In one embodiment, the earplug device may use a balanced armature, which is a sound transducer design that increases electrical efficiency. The piezoelectric sensor and/or the balanced armature may be used to handle tight space constraints and to minimize energy consumption. In one embodiment, the speaker 103 may be designed by a variety of different technologies, such as, and is not limited to, electromagnetics and thermo-acoustics. In one embodiment, the speaker 103 may serve as a buzzer and may vibrate instead of produce sound.

The speaker 103 is positioned as deep into an ear canal as possible to further minimize energy consumption. The cable 109 goes from the speaker 103 through the earplug 105 and to the electronics base 107. This allows for replacement of an actual earplug component with the replaceable foam earplug 119 for hygienic purposes.

Standard foam earplugs for noise reduction are usually rolled up to fit into the ear canal. In one embodiment, a custom foam (polyurethane) earplug 105 with a small axial hole where the cable 109 passes through may be used. The custom foam (polyurethane) earplug 105 minimizes noise that goes through the earplug into the ear canal in order to achieve a higher noise reduction rating ("NRR"). The NRR is a unit of measurement that determines effectiveness of hearing protection devices to decrease sound exposure in an environment. A higher NRR indicates a greater potential for noise reduction. In another embodiment, silicone earplugs may be used for greater durability.

The electronics base 107 is comprised of a housing. In one embodiment, the housing may be made of smooth plastic to resist the tendency of the earplug to catch on an edge and be pulled out of the ear. The housing is ergonomically designed to distribute any load evenly over an outer ear.

The sensors 111, the wireless transmission module 113, the processor 117, and the battery 115 are brought together on a central printed circuit board which is placed inside the housing of the electronics base 107. In one embodiment, the housing may have a threaded hole that connects to an axial jack through which the speaker 103 connects to electronic components. In one embodiment, a speaker wiring may have a certain length so that it can traverse through a length of the earplug.

In one embodiment, the earplug device utilizes Bluetooth low energy ("BLE") as the wireless transmission module 113 to minimize energy consumption. With the advent of BLE technology, there is a growing trend of imaginative "smart" devices, enabling basic objects to have additional functionality. BLE technology uses less power consumption within a similar communication range. This means that while similar earplug device designs require nightly recharging, the user of this earplug device does not have to do so. A ping rate of a wireless signal should be very low as to preserve energy because a one-second delay on the alarm is inconsequential to an alarm clock functionality. "Ping" is an acronym for Packet Internet or Inter-Network Groper. The ping rate is a response time for a system to speak to a server. The present teachings disclose that a lower ping rate is better than a higher ping rate as it entails significant energy savings.

In one embodiment, the battery 115 may be a traditional coin cell battery because of the high internal resistance and low maximum current values. Using the traditional coin cell battery takes advantage of BLE's low current requirements, which allows for prolonged usage on a single battery.

The processor 117 may be integrated into a system-on-chip solution package with the wireless transmission module 113. In one embodiment, a simple microcontroller may receive a signal from the wireless transmission module 113 and output a corresponding electrical signal.

In one embodiment, the sensors 111 for acquiring biometric data may be in the form of the accelerometer 121, a temperature sensor, or a photo sensor. Movements of people, temperature, and heart rate vary predictably through different sleep phases. The sensors 111 correlate the movement-temperature data to analyze and predict when the user is in a certain stage of sleep. This information would be used in a form of a bio-clock, where users would be awakened in a pre-determined time frame when they are in a lighter phase of sleep.

As indicated above, in one embodiment, the accelerometer 121 acts as one of the sensors 111. The accelerometer 121 is a device that measures acceleration. The accelerometer 121 tracks head movements during sleep to monitor REM cycles of the user and wake him up during a lighter phase of sleep. People wake up feeling groggy if they awaken during REM sleep. Using the accelerometer 121 prevents waking the user up during his REM cycle.

The at least one electronic device 123 is any device with advanced computing and wireless connectivity capabilities, such as smartphones.

Those skilled in the art will appreciate that the present teachings may be practiced with other system configurations, including hand-held devices, multiprocessor systems, microprocessor-based or programmable consumer electronics, network PC's, minicomputers, mainframe computers, and the like. The present teachings may also be practiced in distributed computing environments where tasks are performed by remote processing devices that are linked through a communications network. In a distributed computing environment, program modules may be located in both local and remote memory storage devices.

The computer described herein above may operate in a networked environment using logical connections to one or more remote computers. These logical connections can be achieved using a communication device that is coupled to or be a part of the computer; the present teachings are not limited to a particular type of communications device. The remote computer may be another computer, a server, a router, a network PC, a client, a peer device or other common network node, and typically includes many or all of the elements described above relative to the computer. The logical connections include a local-area network (LAN) and a wide-area network (WAN). Such networking environments are commonplace in office networks, enterprise-wide computer networks, intranets and the Internet, which are all types of networks.

When used in a LAN-networking environment, the computer is connected to the local network through a network interface or adapter, which is one type of communications device. When used in a WAN-networking environment, the computer typically includes a modem, a type of communications device, or any other type of communications device for establishing communications over the wide area network, such as the Internet.

The foregoing description illustrates exemplary implementations, and novel features, of aspects of an earplug device that communicates with at least one electronic device. Alternative implementations are suggested, but it is impractical to list all alternative implementations of the present teachings. Therefore, the scope of the presented disclosure should be determined only by reference to the appended claims, and should not be limited by features illustrated in the foregoing description except insofar as such limitation is recited in an appended claim. While the above description has pointed out novel features of the present disclosure as applied to various embodiments, the skilled person will understand that various omissions, substitutions, permutations, and changes in the form and details of the present teachings illustrated may be made without departing from the scope of the present teachings.

Each practical and novel combination of the elements and alternatives described hereinabove, and each practical combination of equivalents to such elements, is contemplated as an embodiment of the present teachings. Because many more element combinations are contemplated as embodiments of the present teachings than can reasonably be explicitly enumerated herein, the scope of the present teachings is properly defined by the appended claims rather than by the foregoing description. All variations coming within the meaning and range of equivalency of the various claim elements are embraced within the scope of the corresponding claim. Each claim set forth below is intended to encompass any apparatus or method that differs only insubstantially from the literal language of such claim, as long as such apparatus or method is not, in fact, an embodiment of the prior art. To this end, each described element in each claim should be construed as broadly as possible, and moreover should be understood to encompass any equivalent to such element insofar as possible without also encompassing the prior art. Furthermore, to the extent that the term "includes" is used in either the detailed description or the claims, such term is intended to be inclusive in a manner similar to the term "comprising."

What is claimed is:

1. An earphone comprising:
   an earplug,
   a processor,
   a wireless interface,
   a battery,
   a speaker, and
   a sensor; wherein
   when the earphone is located in a user's ear, the sensor detects data indicative of the state of sleep of the user and provides that data to the processor, and
   the processor is configured to cause the speaker to provide sound to the user based on the sensor data.

2. The earphone of claim 1, wherein the processor is configured to cause the speaker to provide a sound when the sensor data indicates that the user is in REM sleep.

3. The earphone of claim 2, wherein the sensor comprises an accelerometer, and the determination that the user is in REM sleep is based on head movement detected by the accelerometer.

4. The earphone of claim 1, wherein the sensor comprises one or more of a movement sensor, a temperature sensor, or a heart rate sensor.

* * * * *